(12) United States Patent
Pleil et al.

(10) Patent No.: US 8,079,468 B2
(45) Date of Patent: Dec. 20, 2011

(54) SURGICAL SCREW CONTAINER

(75) Inventors: Thomas Pleil, Bad Duerrheim (DE);
Dieter Weisshaupt, Immendingen (DE);
Markus Nesper, Tuttlingen (DE)

(73) Assignee: Aesculap AG, Tuttlingen (DE)

( * ) Notice: Subject to any disclaimer, the term of this patent is extended or adjusted under 35 U.S.C. 154(b) by 397 days.

(21) Appl. No.: 12/002,312

(22) Filed: Dec. 14, 2007

(65) Prior Publication Data

US 2008/0149511 A1 Jun. 26, 2008

Related U.S. Application Data

(63) Continuation of application No. PCT/EP2006/005458, filed on Jun. 8, 2006.

(30) Foreign Application Priority Data

Jun. 22, 2005 (DE) .......................... 10 2005 030 553

(51) Int. Cl.
*B65D 85/24* (2006.01)
*B65D 71/00* (2006.01)
*A61B 17/06* (2006.01)

(52) U.S. Cl. ......... 206/339; 206/438; 206/570; 206/572

(58) Field of Classification Search .................. 206/339, 206/438–440, 557–567, 488, 349, 234, 372, 206/373, 570–572
See application file for complete search history.

(56) References Cited

U.S. PATENT DOCUMENTS

| | | | |
|---|---|---|---|
| 2,835,377 A | 5/1958 | May et al. | |
| 5,150,788 A | 9/1992 | Weissman | |
| 5,344,024 A * | 9/1994 | Cohu | ............................ 206/526 |
| 5,445,641 A | 8/1995 | Frigg et al. | |
| 5,676,254 A * | 10/1997 | Cheng et al. | ................... 206/751 |
| 5,690,223 A | 11/1997 | Wood | |
| 5,732,821 A * | 3/1998 | Stone et al. | .................... 206/370 |
| 5,887,715 A * | 3/1999 | Vasudeva | ....................... 206/373 |
| 5,915,553 A * | 6/1999 | Brown et al. | .................. 206/372 |
| 6,328,746 B1 | 12/2001 | Gambale | |
| 6,592,578 B2 * | 7/2003 | Henniges et al. | ................ 606/27 |
| 6,830,573 B2 * | 12/2004 | Strong et al. | ................... 606/300 |
| 7,007,798 B2 | 3/2006 | Happonen et al. | |
| 2005/0216015 A1 * | 9/2005 | Kreidler | .......................... 606/73 |
| 2005/0241974 A1 * | 11/2005 | Chen | ............................. 206/379 |
| 2007/0150057 A1 | 6/2007 | Kurz et al. | |

FOREIGN PATENT DOCUMENTS

| | | |
|---|---|---|
| BE | 1005149 | 5/1993 |
| CH | 684820 | 1/1995 |
| DE | 203 18 732 | 2/2004 |

(Continued)

*Primary Examiner* — J. Gregory Pickett
*Assistant Examiner* — Kaushikkumar Desai
(74) *Attorney, Agent, or Firm* — Lipsitz & McAllister, LLC

(57) ABSTRACT

In order to improve a surgical screw container comprising a receiving part and a closure part mounted thereon so as to be movable, wherein the receiving part has at least two screw receptacles for accommodating at least two bone screws, wherein the closure part can be brought relative to the receiving part into at least one closure position, in which none of the screw receptacles is accessible for the introduction or removal of a bone screw, such that any loss of screws from the screw container can be practically ruled out it is suggested that the closure part can be brought from the at least one closure position into at least two removal positions, in each of which only a single screw receptacle is accessible for the introduction or removal of a single bone screw.

58 Claims, 7 Drawing Sheets

FOREIGN PATENT DOCUMENTS

| | | |
|---|---|---|
| DE | 20 2004 017 593 | 3/2005 |
| EP | 0 578 778 | 1/1997 |
| EP | 1 258 437 | 11/2002 |
| WO | 01/62136 | 8/2001 |

\* cited by examiner

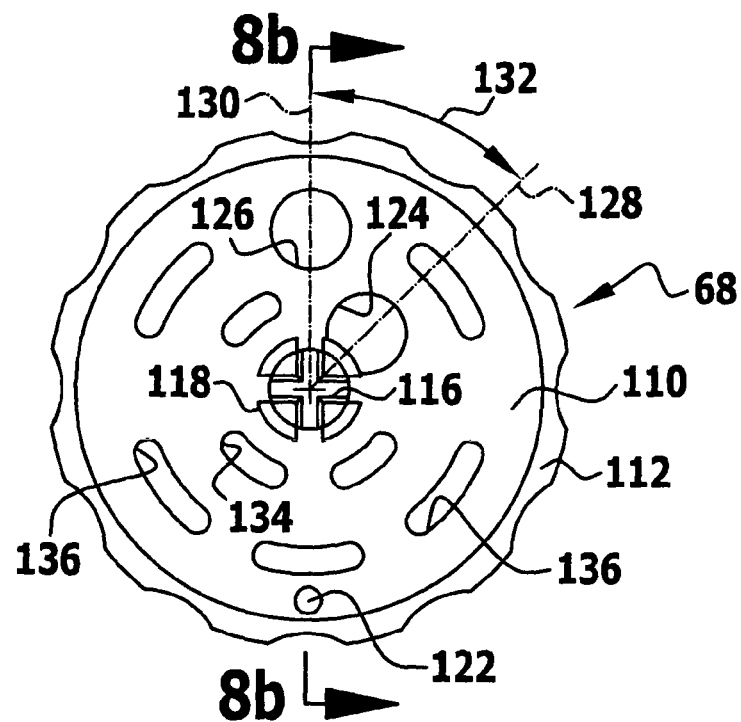
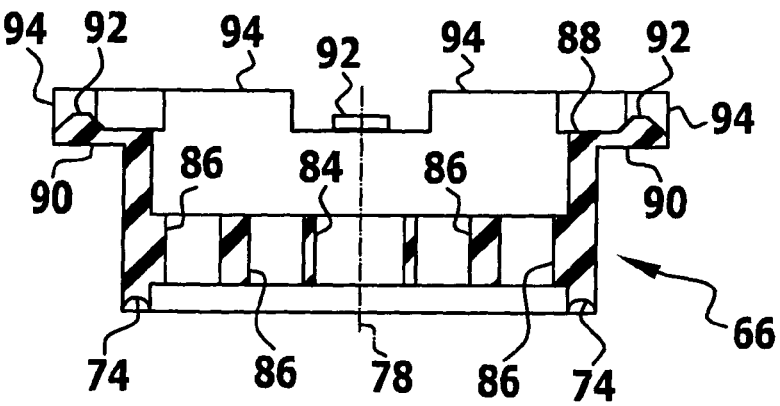
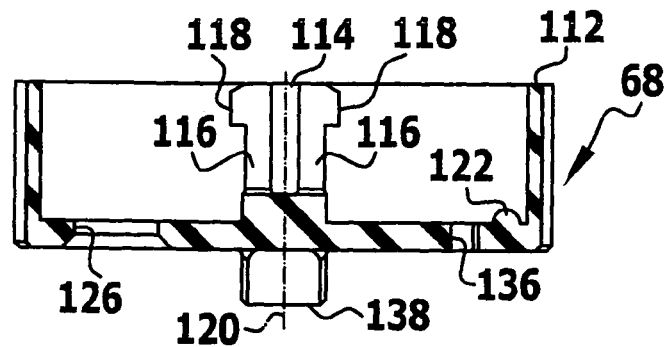

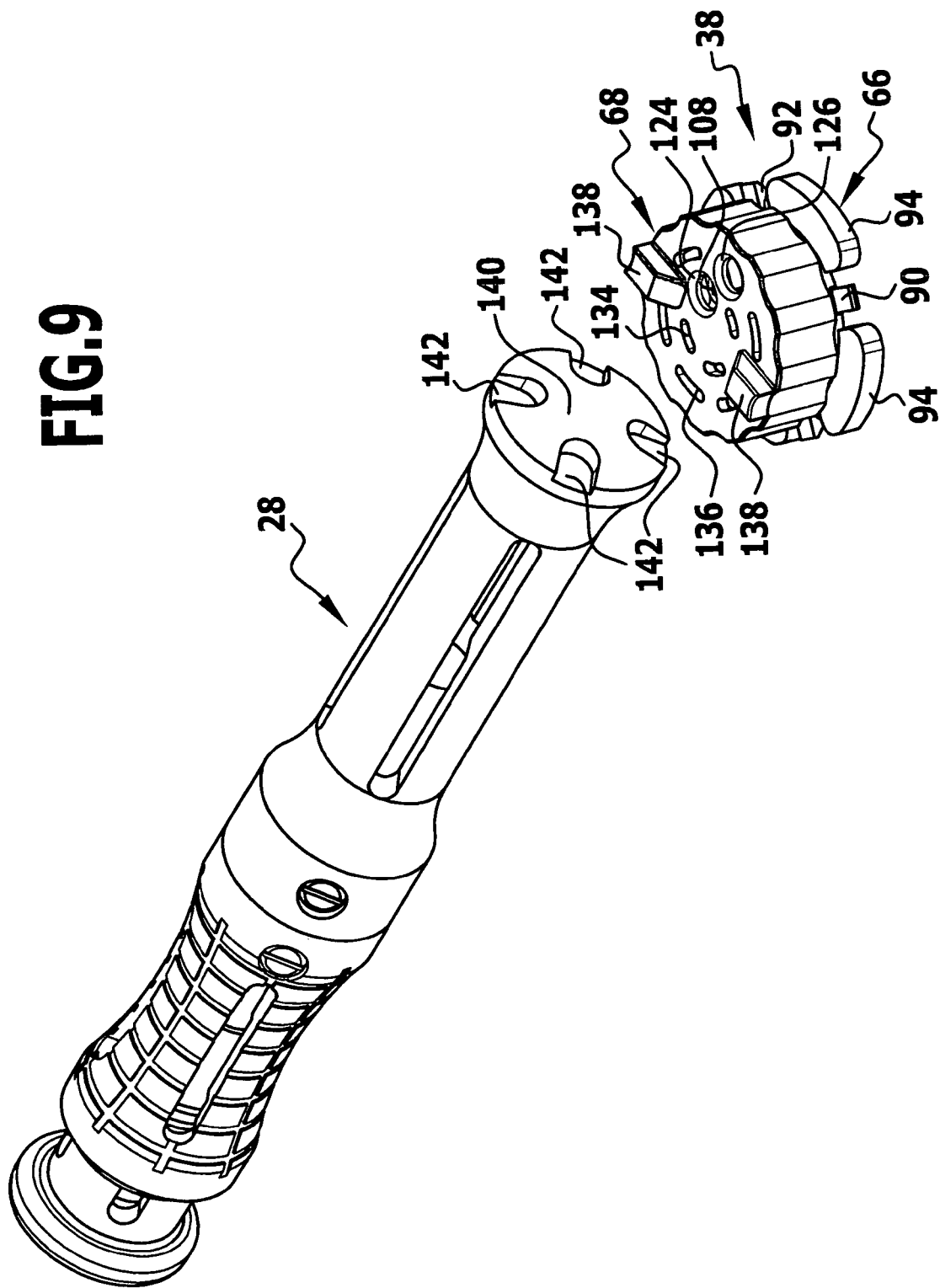

SURGICAL SCREW CONTAINER

This application is a continuation of International application No. PCT/EP2006/005458 filed on Jun. 8, 2006.

The present disclosure relates to the subject matter disclosed in International application No. PCT/EP2006/005458 of Jun. 8, 2006 and German application No. 10 2005 030 553.9 of Jun. 22, 2005, which are incorporated herein by reference in their entirety and for all purposes.

BACKGROUND OF THE INVENTION

The present invention relates to a surgical screw container comprising a receiving part and a closure part mounted thereon so as to be movable, wherein the receiving part has at least two screw receptacles for accommodating at least two bone screws, wherein the closure part can be brought relative to the receiving part into at least one closure position, in which none of the screw receptacles is accessible for the insertion or removal of a bone screw.

In surgery, small, flat bone plates, which are fixed to the bone, for example, with self-cutting and self-boring screws, are used, in particular, for the fixing of bone fragments or artificial bone opercula in the cranial region. The bone screws used for this purpose are, generally, very small and so they can be handled only with difficulty and can easily become lost. They are, therefore, usually made available for use in surgery in a surgical screw container of the type described at the outset.

In the case of the known screw containers, the fact that all the screw receptacles are freely accessible after removal of the closure part has proven to be disadvantage. As a result, all the screws found in the screw container can be accessed at the same time but there is also the risk of these screws being able to fall out of the screw container, for example, when the screw container tilts over. Since, in addition, exact records must be kept during a surgical procedure as to what instruments and, where applicable, also what implants have been used, it is necessary to search for a lost bone screw for such a time until it is found again. It is possible only in this way to avoid any instruments or implant parts unintentionally being left in the body of a patient.

Therefore, it would be desirable to provide a surgical screw container of the described type at the outset so that any loss of screws from the screw container can be ruled out.

SUMMARY OF THE INVENTION

In accordance with the invention, it is suggested in a surgical screw container of the type described at the outset, that the closure part can be brought from the closure position into at least two removal positions, in each of which only a single screw receptacle is accessible for the insertion or removal of a single bone screw.

The surgical screw container according to the invention ensures that only one screw receptacle is freely accessible in each removal position. So that the screw can be removed from the screw container, the closure part must, first of all, be brought relative to the receiving part from the at least one closure position, i.e., from one closure position or from several closure positions into one or several removal positions. Only then is access to one of the at least two screw receptacles possible. All the other screw receptacles are, however, not accessible. As a result, none of the screws located in the other screw receptacles can fall out of the screw container. Furthermore, it is to be noted that the surgical screw container can also serve to accommodate other securing elements or tools, for example, surgical needles or tool inserts, so-called "bits".

The construction and the production of the screw container become particularly simple when the screw receptacles are designed in the form of insert bores or blind-hole bores in a basic member of the receiving part. The screw can be inserted into the insert bores or blind-hole bores, in particular, with a screw body provided with an external thread first so that a head of the screw protrudes out of these bores.

A transition from the at least one closure position into the at least one removal position and vice versa becomes particularly simple when the closure part is mounted on the receiving part so as to be rotatable about an axis of rotation.

The construction of the screw container is simplified further when longitudinal axes of the screw receptacles extend parallel to the axis of rotation.

Individual access to a single screw receptacle is simplified when the at least two screw receptacles are arranged concentrically around the axis of rotation.

The at least two screw receptacles are advantageously arranged on at least two concentric circles around the axis of rotation. As a result, considerably more screw receptacles can be provided in the screw container than is possible with an arrangement of the screw receptacles on only one circle concentric to the axis of rotation.

In order to be able to connect the closure part securely to the receiving part and, where applicable, to release it again therefrom in a simple manner, it is favorable when the closure part can be connected to the receiving part in a snap-in manner so as to be movably mounted thereon. A snap-in connection has, in addition, the advantage that the fact that the connecting position of receiving part and closure part has been taken up can generally not only be felt but also heard by an operator.

In accordance with a preferred embodiment of the invention, it may be provided for the receiving part and the closure part to each bear a coupling element for their movable mounting on one another and these coupling elements can be brought into engagement with one another. As a result of the two coupling elements, a connection can be realized between the receiving part and the closure part in a simple manner.

In order to keep the closure part and the receiving part secure in a coupling position and movable relative to one another and on one another in a simple manner, it is advantageous when the two coupling elements are rotatable relative to one another in a coupling position and are held on one another by means of a snap-in connection.

The construction of the screw container and its parts is simplified further when one of the two coupling elements is a coupling pin and when the other coupling element is a pin receptacle corresponding to the coupling pin.

It is particularly favorable when the coupling pin defines the axis of rotation. The coupling pin therefore serves, on the one hand, for connecting the receiving part to the closure part; on the other hand, it also forms a bearing shaft.

In order to be able to remove a screw from the screw container in one of the removal positions in a simple manner, it is particularly favorable when the closure part has at least one removal opening and when the at least one removal opening frees a single screw receptacle at least in one of the at least two respective removal positions. For example, two or even more removal openings can also be provided, wherein, however, only a single screw receptacle is freely accessible in each respective removal position.

The construction and the production of the closure part are simplified when it has a cover plate for covering the screw receptacles at least partially and when the at least one removal opening is designed in the form of a passage in the cover plate.

The shape of the passage can be adapted, in particular, to the shape of the screw receptacle and/or be similar to it. In the case of a round or cylindrical screw container, the cover plate can have the form of a flat disk.

The production of the closure part becomes particularly simple when the passage is a bore.

A plurality of removal positions can be taken up in a particularly simple manner when the at least one removal opening is arranged concentrically around the axis of rotation. It is then possible to transfer between one and several removal positions and/or closure positions in a simple manner by rotating the closure part relative to the receiving part.

In principle, it would be conceivable for longitudinal axes of the screw receptacles to be arranged transversely to the axis of rotation. However, the screw container may be of a considerably more compact design when only one removal opening can be aligned coaxially with one of the respective screw receptacles in each of the plurality of removal positions. Particularly in the case of screw receptacles which are aligned parallel to the axis of rotation, they can all be stored in the screw container parallel to their longitudinal axes and also be inserted and/or removed parallel to their axes.

It is advantageous when a positioning mechanism comprising a plurality of positioning members is provided for the defined positioning of the closure part in at least one closure position and/or in at least one removal position, when at least one of the positioning members is provided on the receiving part and at least one positioning member corresponding to it is provided on the closure part and when at least two positioning members corresponding to one another on the closure part and on the receiving part engage in one another when at least one removal opening of the closure part frees a single screw receptacle in the at least one removal position. It can thus be ensured in a simple manner by means of the positioning device that the closure part takes up a removal position and/or closure position relative to the receiving part in a defined manner. For example, the positioning mechanism can be designed in the form of a snap-in mechanism so that an operator can not only feel but also hear when a closure position and/or a removal position is taken up.

The positioning members preferably comprise positioning projections and positioning recesses. In this way, the construction of the screw member can be simplified further.

A particularly compact construction of the screw member is made possible when the positioning members are arranged concentrically around the axis of rotation. For example, the screw receptacles could, themselves, serve as positioning member, in which a corresponding projection engages.

So that the screw container can accommodate as many screws or tool inserts as possible, it is favorable when the positioning members are arranged at equal angular distances around the axis of rotation. It could also be said that the positioning members are arranged so as to be distributed uniformly in circumferential direction. In this way, a highly symmetric construction of the screw container may be realized, in addition.

In accordance with a preferred embodiment of the invention, it may be provided, in addition, for the receiving part to have an annular edge pointing in the direction towards the closure part and for the edge to bear the positioning members provided on the receiving part. The edge can, on the one hand, serve as a stop for the closure part and, on the other hand, bear the positioning members. The positioning members of the closure part may be brought into engagement with those of the receiving part particularly easily when at least one positioning member is arranged on an underside of the closure part pointing in the direction towards the receiving part. For example, a positioning mechanism with the positioning members arranged on an edge of the receiving part may be formed with a positioning member arranged in such a manner.

It is advantageous when the number of positioning receptacles corresponds to an integral power of the number 2, when the number of positioning projections provided is at the most the same as the number of positioning receptacles and when the angular distance between the positioning receptacles corresponds to the quotient of 3600 and the number of positioning receptacles. For example, four, eight, sixteen or thirty-two positioning receptacles and, at the most, an equal number of positioning projections can be provided, wherein an angular distance between the positioning receptacles is then 90°, 45°, 22.5° and 11.25°, respectively.

In order to keep the construction of the surgical screw container as simple as possible and, nevertheless, be able to store as many screws or instrument inserts in the container as possible, it is favorable when at least two removal openings are provided which are arranged on at least two radial rays proceeding from the axis of rotation and when the at least two radial rays form between them an angle of rotation. It may be ensured by selecting the angle of rotation accordingly or arranging the screw receptacles accordingly that only one screw receptacle is freely accessible per removal position for the insertion and/or removal of a screw.

The angle of rotation advantageously corresponds to an integral multiple of the angular distance between the positioning members on the closure part and/or on the receiving part. As a result, it is possible, for example, to bring the positioning members arranged on the two parts into engagement in each or in every second angular position of the closure part relative to the receiving part so that removal positions and/or closure positions are taken up in a defined manner.

It is favorable when at least two removal openings, which are at different distances from the axis of rotation, are provided and when the angle of rotation formed by the radial rays, on which the removal openings are arranged, is 45°. If more than two removal openings arranged on more than two radial rays are provided, the angle of rotation formed can also be smaller than 45°. The angle of rotation formed preferably corresponds to double the angular distance between two positioning members.

In principle, it would be conceivable to use the screw container on its own. However, it is also conceivable to arrange the screw container with additional screw containers for screws of different sizes in a common screw storage device. In order to avoid the possibility of a screw container becoming detached from the screw storage device in an undesired manner, it is favorable when at least one storage device coupling member is provided on the screw container for the releasable connection of the screw container to the surgical screw container storage device for at least one surgical screw container. In this way, a screw container can be connected to the screw container storage device without there being the risk of it becoming detached from the screw container storage device unintentionally. Moreover, a screw container can be interchanged in a simple manner, for example, when larger screws or screws of a different type are required for a surgical procedure.

The construction of the screw container becomes particularly simple when the at least one storage device coupling member comprises a snap-in element for bringing into engagement with a corresponding snap-in element of the screw container storage device.

So that the screw container can also be releasably connected to a screw container storage device in different positions, it is favorable when several storage device coupling members are provided which are distributed uniformly over the circumference of the screw container. For example, a screw container having altogether a fourfold symmetry can be equipped with four storage device coupling members distributed over its circumference at an angular distance of 90°.

It is advantageous when the screw container bears at least two coupling projections which protrude in opposite directions, are designed to correspond to two parallel grooves, which point towards one another, of at least one screw container receptacle of a surgical screw container storage device, which can accommodate at least one surgical screw container, and can be inserted into the grooves. In this way, it is possible for the screw container to be held securely on the screw container storage device. Movement of the screw container relative to the screw container storage device is limited to a degree of freedom of movement by the grooves provided.

The construction of the screw container becomes particularly simple when the at least two coupling projections are formed by tongues which are located in one plane and spaced from one another in circumferential direction. For example, four tongues can be provided which can be designed and arranged, in addition, in the form of a clover leaf.

In order to fix the screw container secured on the screw container storage device with the coupling projections so as to be at least temporarily immovable on the screw container storage device, it is favorable when a storage device coupling member of the screw container is arranged between two respective coupling projections. This makes it possible to insert the screw container into the screw container receptacle in different positions and also releasably connect it to the screw container storage device in different positions.

Four different connecting positions are possible between the screw container and a screw container storage device when four coupling projections and four storage device coupling members are provided and when an outer contour of the coupling projections is designed to be concentric to the axis of rotation.

In order to prevent any turning of the screw container in grooves of the screw container storage device, it is favorable when a distance of a tangent touching two spaced coupling projections from the axis of rotation is smaller than a distance of the concentric outer contour of the coupling projections from the axis of rotation. This means that a secant of the coupling projections otherwise defining, altogether, a disk-like outer contour is formed so to speak as a result of the distance of the coupling projections from one another and prevents any turning of the screw container in grooves of the screw container storage device when a distance between groove bases of the grooves is greater than double the distance of the tangent from the axis of rotation but smaller than an external diameter of the concentric outer contour of the coupling projections.

The closure part favorably has wash openings. This makes it possible to prepare the screw container again following a surgical procedure without the screws not used needing to be removed from the screw container.

In order to simplify the production of the closure part, the wash openings are provided in the cover plate.

So that the cleaning not only of the screw container but also of screws or instrument inserts stored therein is improved, it is advantageous when the receiving part comprises a sleeve-like basic member defining a longitudinal direction and at least one web which passes through the basic member transversely to the longitudinal direction and bears the at least two screw receptacles. The sleeve-like basic member can, in particular, be designed in the form of a hollow cylindrical ring which has one or two webs intersecting a longitudinal axis of the basic member.

It is favorable when at least two intersecting webs are provided and when the pin receptacle is arranged at the point of intersection of the two webs. As a result, the stability of the screw container is increased, on the one hand, and, on the other hand, a possibility is created in a simple manner of connecting the receiving part to the closure part, in particular, by providing a coupling pin on the closure part which corresponds to the pin receptacle.

So that a maximum volume of the screw container can, as far as possible, be used for accommodating screws or instrument inserts, the coupling projections preferably project radially outwards from the sleeve-like basic member in a flange-like manner.

In order to keep not only the construction of the screw container but also a construction of a screw container storage device as compact as possible, it is advantageous when the storage device coupling members project radially outwards from the sleeve-like basic member in a flange-like manner.

In principle, it would be conceivable to move the closure part relative to the receiving part by hand. However, in order to prevent, as far as possible, any damage to surgical gloves worn by surgeons during a surgical procedure, it is favorable when the closure part bears at least one tool coupling member for an actuating tool for turning the closure part relative to the receiving part. If, for example, the receiving part is inserted with coupling projections and, possibly, storage device coupling members present, in addition, into a screw container receptacle of a screw container storage device, the closure part can then be turned relative to the receiving part in a simple manner by means of the actuating tool.

The construction of the screw container becomes particularly simple when the at least one tool coupling member is a projection projecting from the cover plate of the closure part. Such a projection also serves alternatively as a point of engagement in order to be able to turn the closure part relative to the receiving part by hand.

So that it can be ensured that the at least one tool coupling member can be brought into engagement with the actuating tool in a defined manner, it is favorable when two tool coupling members, which are located diametrically opposite one another in relation to the axis of rotation, are provided. As a result, torque can be transferred symmetrically to the closure part.

In order to be able to prepare, in particular, to sterilize the screw container together with the screws contained therein, it is favorable when the screw container is produced from a sterilizable plastic.

So that it is immediately apparent how many screw receptacles of the screw container are filled and which ones, it is advantageous when the closure part is produced from a transparent material.

A bone screw is favorably arranged in each screw receptacle. The screw container therefore comprises, in addition, the bone screws or tool inserts contained in the screw receptacles.

In addition, a surgical screw container storage device for at least one of the surgical screw containers described above is suggested, the screw container storage device has at least one screw container receptacle, into which the at least one screw container can be inserted at least partially. This makes it possible to combine one or more screw containers, for example, screw containers which are equipped with screws of different sizes. As a result, screws of different sizes can be made available for a surgical procedure, wherein the advantageous developments of the screw container described above enable only a single screw or an instrument insert to be respectively removed from the screw container. This does, however, also mean that only a single screw or an instrument insert can be respectively removed from the entire screw container storage device having several screw containers. Furthermore, this has the advantage that a screw which has already been removed or an instrument insert can be returned to the screw container provided for it, namely once the desired screw container is brought into the required removal position for the screw receptacle provided for accommodating the screw.

Screw containers may be connected to the screw container storage device particularly easily when the at least one screw container can be pushed into the screw container receptacle.

The surgical screw container storage device favorably comprises at least one of the screw containers according to the invention described above. The screw container storage device and the at least one screw container therefore form a unit. For example, the screw container storage device can, therefore, already be presented for use in surgery with one or several screw containers.

It is advantageous when the at least one surgical screw container can be connected to the screw container storage device in a snap-in manner. This simplifies not only the construction of the screw container but also that of the screw container storage device. It is conceivable, in particular, to produce both parts from a plastic material by way of injection molding.

In order to ensure that one or more screw containers cannot become detached from the screw container storage device in any undesired manner, it is favorable when the at least one surgical screw container is connected to the screw container storage device in a storage position, in which the at least one screw container is introduced completely into the screw container receptacle. The screw container can, in particular, also be released again from the screw container storage device in order to move it out of the storage position.

So that the screw container and the screw container storage device can be connected in the storage position in a simple manner, it is advantageous when the at least one screw container and the screw container storage device each bear a storage device coupling member, these members being in engagement in the storage position. A connection between the screw container and the screw container storage device results, therefore, in the storage position, namely when the respective storage device coupling members are in engagement.

In order to obtain a releasable connection between the screw container and the screw container storage device in a simple manner, it is favorable when one of the two storage device coupling members is designed as a snap-in element in the form of a flexibly mounted snap-in nose and when the other storage device coupling member is designed as a snap-in element in the form of a recess interacting with the snap-in nose. The recess can, for example, also be designed in the form of an opening, in which the snap-in nose can engage entirely or partially in the storage position.

So that screw containers are held securely in the storage position in each screw container receptacle, a storage device coupling member of the screw container storage device is advantageously associated with each screw container receptacle.

Screw containers may be connected to the screw container storage device easily and reliably when the screw container receptacles comprise coupling receptacles in the form of two respective parallel grooves which point towards one another and into which corresponding coupling projections of the at least one screw container can be inserted. It would also be conceivable for the parallel grooves to point away from one another so that corresponding storage device coupling members of the at least one screw container engage around the screw container receptacle at least partially.

Furthermore, in accordance with the invention, a surgical supply box for surgical implants and/or surgical tools is suggested, comprising several compartments for accommodating surgical implants and/or instruments and/or surgical tools in that at least one compartment is provided for accommodating one of the screw container storage devices according to the invention and described above. The screw container storage device according to the invention therefore forms part of a surgical supply box, in which some or all of the instruments, tools and/or implants required for a surgical procedure are contained. This makes it possible to place all the parts required for the preparation of a specific surgical procedure in the surgical supply box. This can preferably be sterilized so that the supply box which has been prepared and equipped can be sterilized prior to the operation.

So that the screw container can be brought from the at least one closure position into at least one removal position, it is favorable when the supply box has at least one receptacle for a screwdriver and/or a screwdriver handle. A bone screw may, on the one hand, be screwed, for example, into a bone with these tools and, on the other hand, the closure part can be moved relative to the receiving part with a handle end configured accordingly.

The supply box preferably comprises at least one screwdriver and/or a screwdriver handle which has a proximal end which bears a tool receptacle for the purpose of engagement with a tool coupling member of the closure part of one of the screw containers described above. The closure part can be moved relative to the receiving part in a simple manner with the screwdriver or the screwdriver handle in order to transfer the closure part from the at least one closure position into the at least one removal position and to remove a screw or an instrument insert from the screw container.

The tool receptacle preferably comprises at least two recesses which are located diametrically opposite one another and point in a proximal direction. It is possible with such a tool receptacle to accommodate two tool coupling members which are located diametrically opposite one another in relation to the axis of rotation of the screw container and turn the closure part relative to the receiving part.

In order to be able to make the desired instruments, tools and/or implants available in an orderly manner for a surgical procedure and be able to remove them easily, it is advantageous when at least some of the compartments are designed to essentially correspond to an outer contour of the implants, instruments, tools or screw container storage devices stored therein.

The following description of a preferred embodiment of the invention serves to explain the invention in greater detail in conjunction with the drawings.

BRIEF DESCRIPTION OF THE DRAWINGS

FIG. 7: shows a view of a closure part of a screw container from below;

FIG. 8a: shows a sectional view along line 8a-8a in FIG. 6;

FIG. 8b: shows a sectional view along line 8b-8b in FIG. 7; and

FIG. 9: shows a perspective view of a screw container with a screwdriver handle.

DETAILED DESCRIPTION OF THE INVENTION

Figure 1:
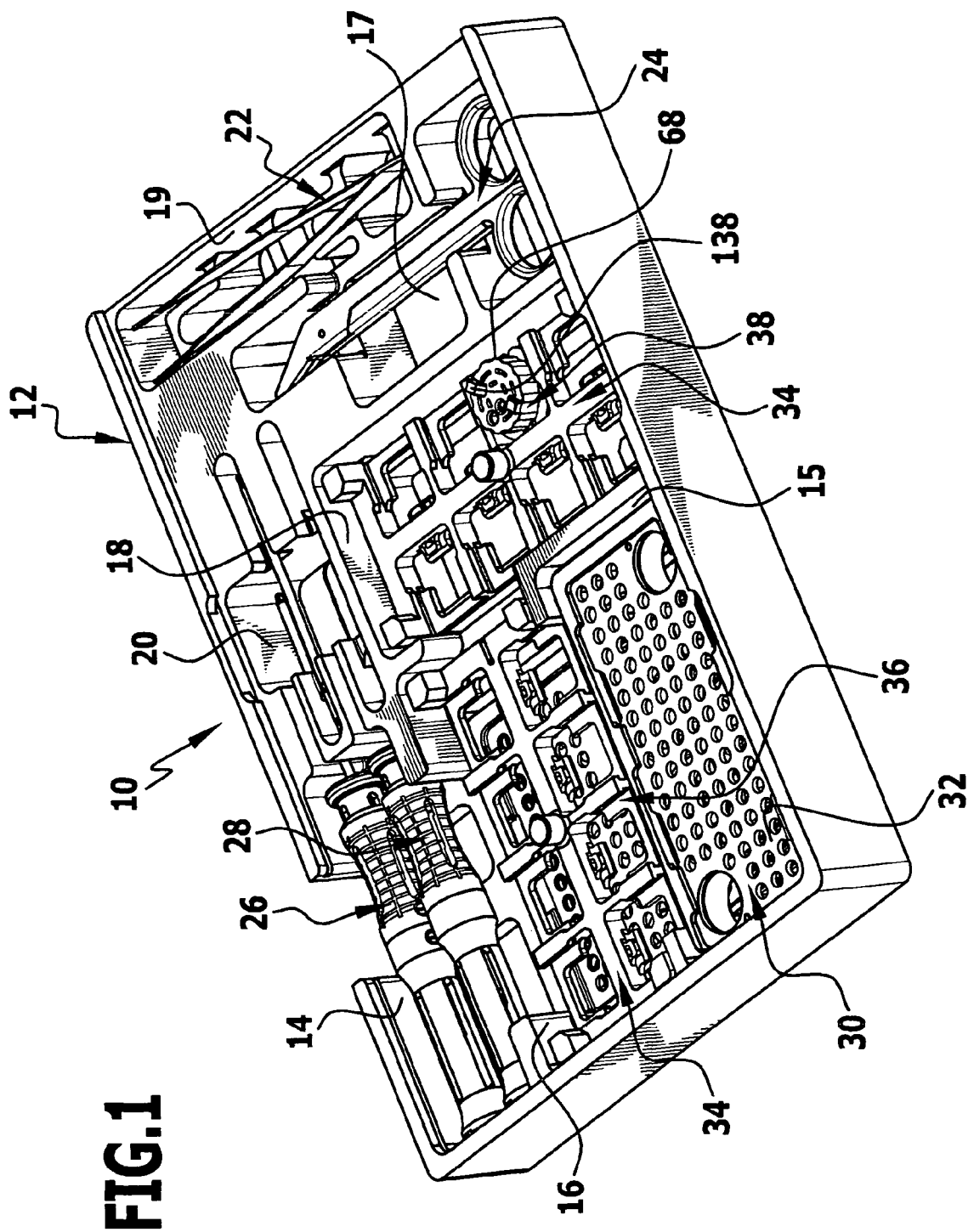
FIG. 1: shows a perspective view of an equipped surgical supply box.

In FIG. 1, a surgical supply box provided altogether with the reference numeral 10 is provided and this comprises a container tray 12 which is essentially in the shape of a parallelepiped and has several compartments of different shapes which are provided in FIG. 1 by way of example with the reference numerals 14, 15, 16, 17, 18, 19 and 20.

The compartments 14 to 20 specified by way of example are shaped in such a manner that surgical instruments, for example, forceps provided altogether with the reference numeral 22 or a pair of scissors provided altogether with the reference numeral 24 can be stored in the respective compartments, for example, the forceps 22 in the compartment 19 or the pair of scissors 24 in the compartment 17 and can be removed in a simple manner. Furthermore, a screwdriver 26 and a screwdriver handle 28, which can be equipped as required with different screw inserts for bone screws, are arranged in the compartment 14. Furthermore, the supply box 10 comprises various storage devices, for example, a storage device 30 for small parts arranged in the compartment 15 and having a perforated displaceable cover 32. The compartments 16 and 18 serve to accommodate respective screw container storage devices 34 which each have 8 screw container receptacles 36 of an essentially identical design, each for accommodating a can-shaped screw container 38.

Figure 2:
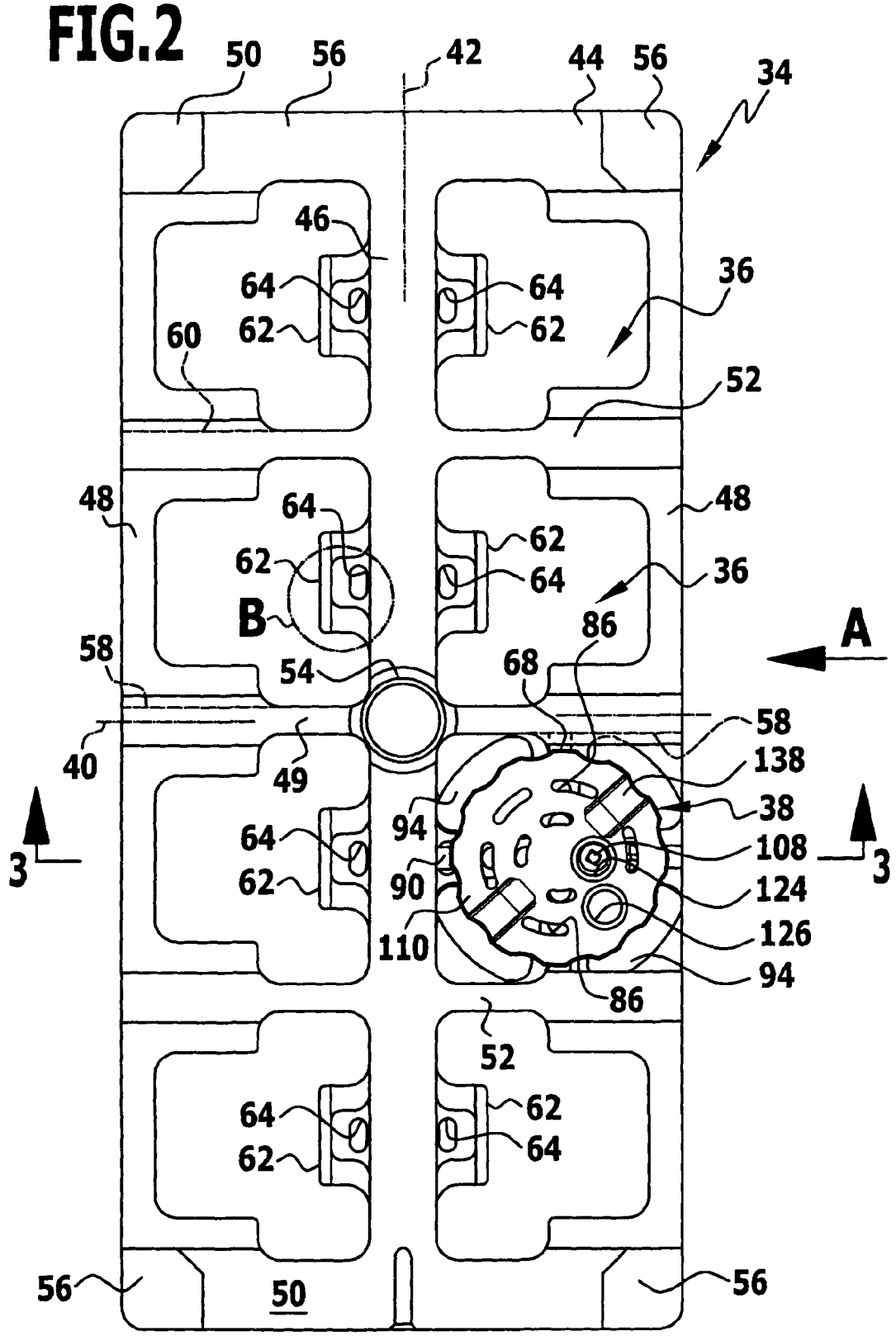
FIG. 2: shows a plan view of a screw container storage device with a screw container in the storage position.
Figure 3:
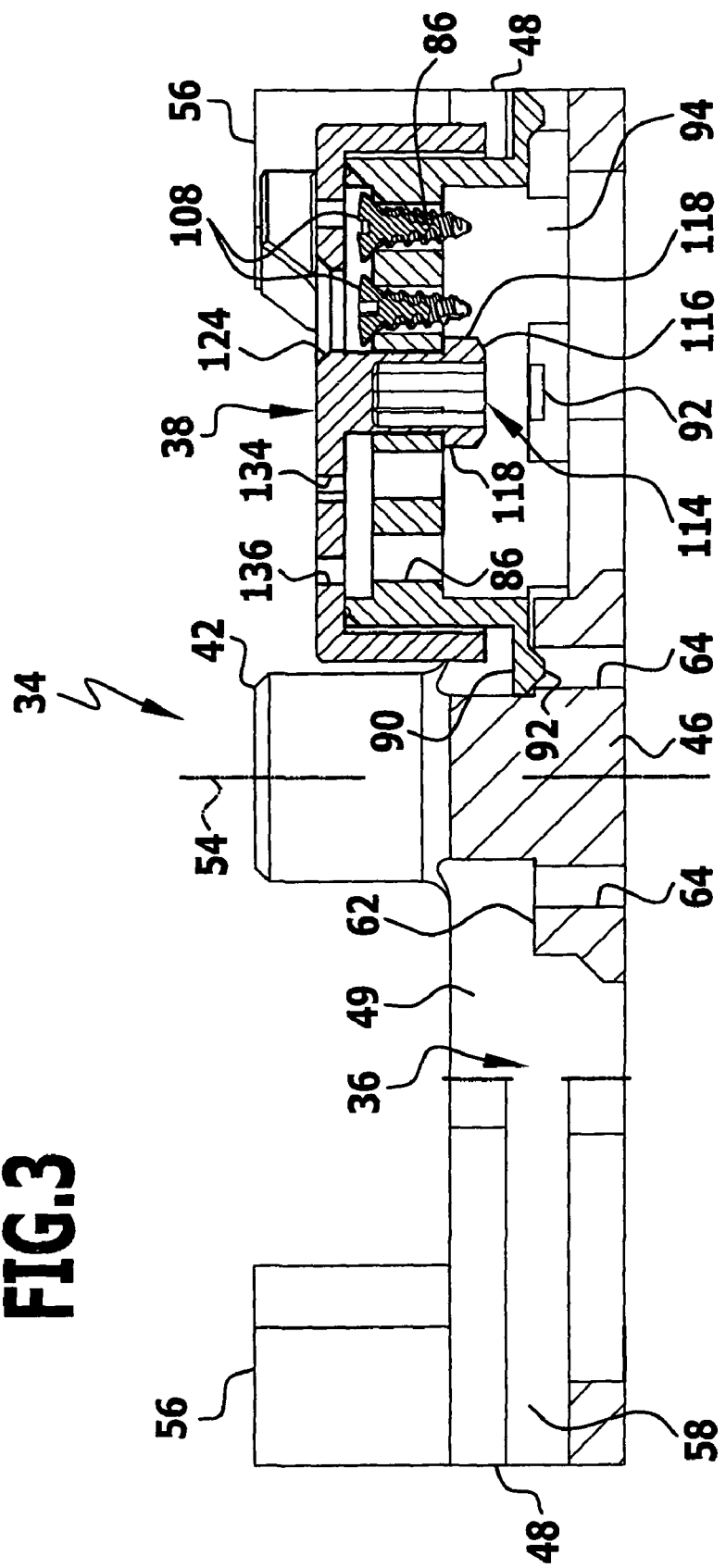
FIG. 3: shows a sectional view along line 3-3 in FIG. 2.
Figure 4:
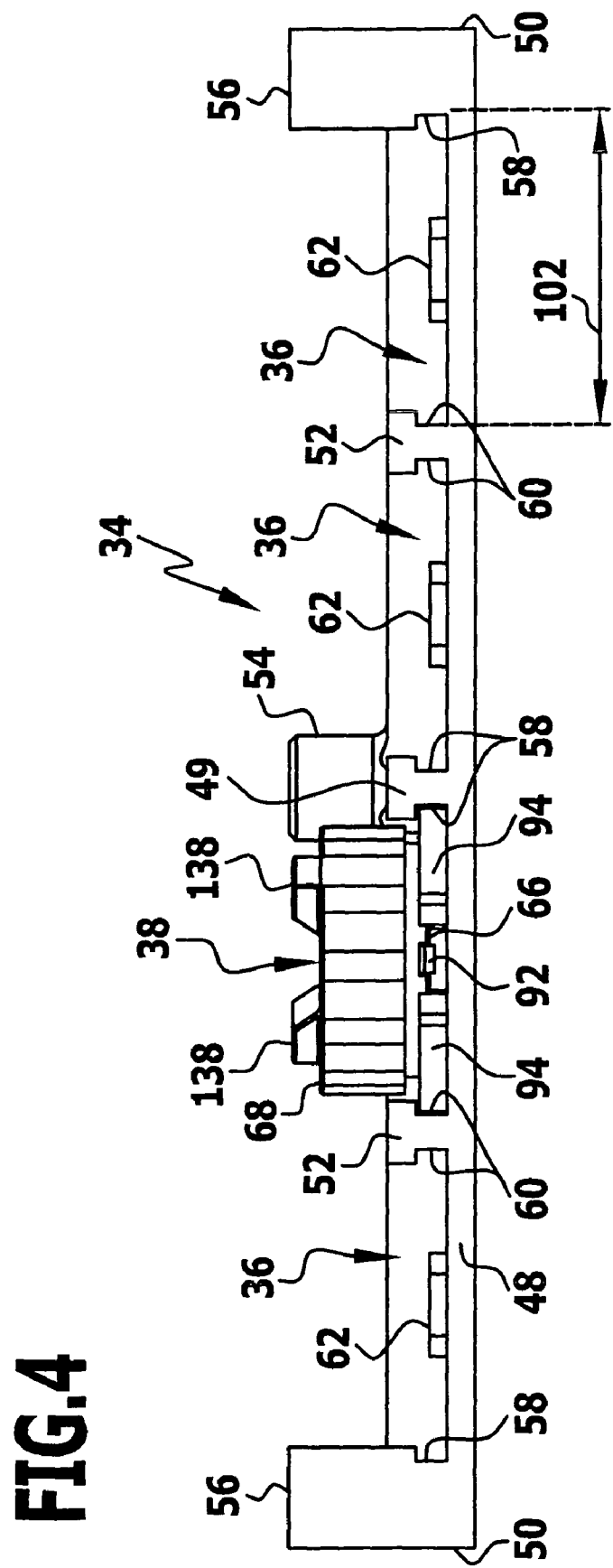
FIG. 4: shows a side view of the screw container storage device in FIG. 2 in the direction of arrow A.
Figure 5:
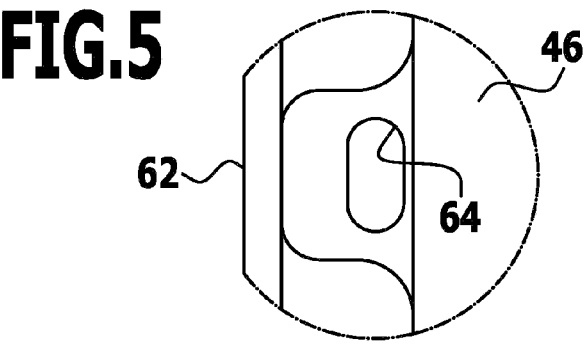
FIG. 5: shows an enlarged view of the section B in FIG. 2.

The screw container storage device 34 described in greater detail in the following in conjunction with FIGS. 2 to 4 is designed in mirror symmetry to two planes of symmetry 40 and 42 intersecting one another at right angles. It comprises an elongated, rectangular frame 44 with a central longitudinal web 46 including the plane of symmetry 42, side webs 48 arranged symmetrically to it as well as a central web 49 including the plane of symmetry 40, outer transverse webs 50 arranged symmetrically to the central web 49 and separating webs 58 arranged between the central web 49 and the transverse webs 50 and running parallel to them. In the point of intersection of the longitudinal web 46 and the central web 49, a holding pin 54 protrudes upwards in the direction of a line of intersection of the planes of symmetry 40 and 42. Spacers 56 essentially in the shape of parallelepipeds likewise protrude upwards in the corners of the frame 44, i.e., in the points of intersection of the side webs 48 and the transverse webs 50.

The screw container receptacles 36 are each limited by a separating web 52, the longitudinal web 46, a side web 48 and either the central web 49 or one of the transverse webs 50. Each screw container receptacle 36 comprises two parallel grooves 58 and 60, the groove bases of which point towards one another and are designed to be parallel to the plane of symmetry 40. Groove side walls of the grooves 58 and 60 define planes which are oriented at right angles not only to the plane of symmetry 40 but also to the plane of symmetry 42. The grooves 58 are respectively arranged in the transverse webs 50 as well as in the central web 49, the grooves 60 in the central web 49. The grooves 58 and 60 each extend over approximately two thirds of the free length of the webs, in which they are arranged, proceeding from an outer edge of the side webs 48.

Projections 62 essentially in the shape of parallelepipeds project from the longitudinal web 46 on both sides of it in the direction towards the side webs 48 and are penetrated by elongated holes 64 in a direction parallel to the line of intersection of the planes of symmetry 40 and 42. The elongated holes 64 form recess-like storage device coupling members for the releasable connection of the screw container storage device to a screw container 38, as illustrated in FIG. 3 and explained in the following in conjunction with the detailed description of the screw container 38.

The screw container 38 illustrated in FIGS. 1 to 4 and 9 will be described in detail in the following in conjunction with FIGS. 6 to 8b.

The screw container 38 is designed in two parts and comprises a receiving part provided with the reference numeral 66 as well as a cover 68 forming a closure part. The receiving part 66 comprises a basic member 70 in the form of a cylindrical sleeve section with an end edge 72 which points upwards and has 16 recesses 74 which form the positioning members of the receiving part 66 and are distributed uniformly over its circumference. They are each arranged on radial rays 76 proceeding from a longitudinal axis 78 of the basic member and offset through an angle 80 which is calculated from the quotient of 360° and the number of recesses 74 and therefore amounts to 22.5°.

Two webs 82, which intersect in the longitudinal axis 78, pass through the basic member 70 transversely to the longitudinal axis 78. A bore 84 forming a pin receptacle is arranged at the point of intersection of the webs 82 and concentrically to the longitudinal axis 78. In addition, two bores forming screw receptacles 86 are provided in the respective webs between the bore 84 and the basic member 70, the longitudinal axes of these bores running parallel to the longitudinal axis 78 and their diameter being somewhat smaller than that of the bore 84.

A snap-in projection 90 projects radially outwards from the basic member 70, from a lower edge 88 of the receiving part 66 in extension of the respective webs 82 and is approximately half as wide as the webs 82. The snap-in projections 90 bear on their undersides snap-in noses 92 which can engage in the elongated holes 64 from above. The snap-in projection 90 with its snap-in nose 92 forms a storage device coupling member of the screw container 38.

Figure 6:
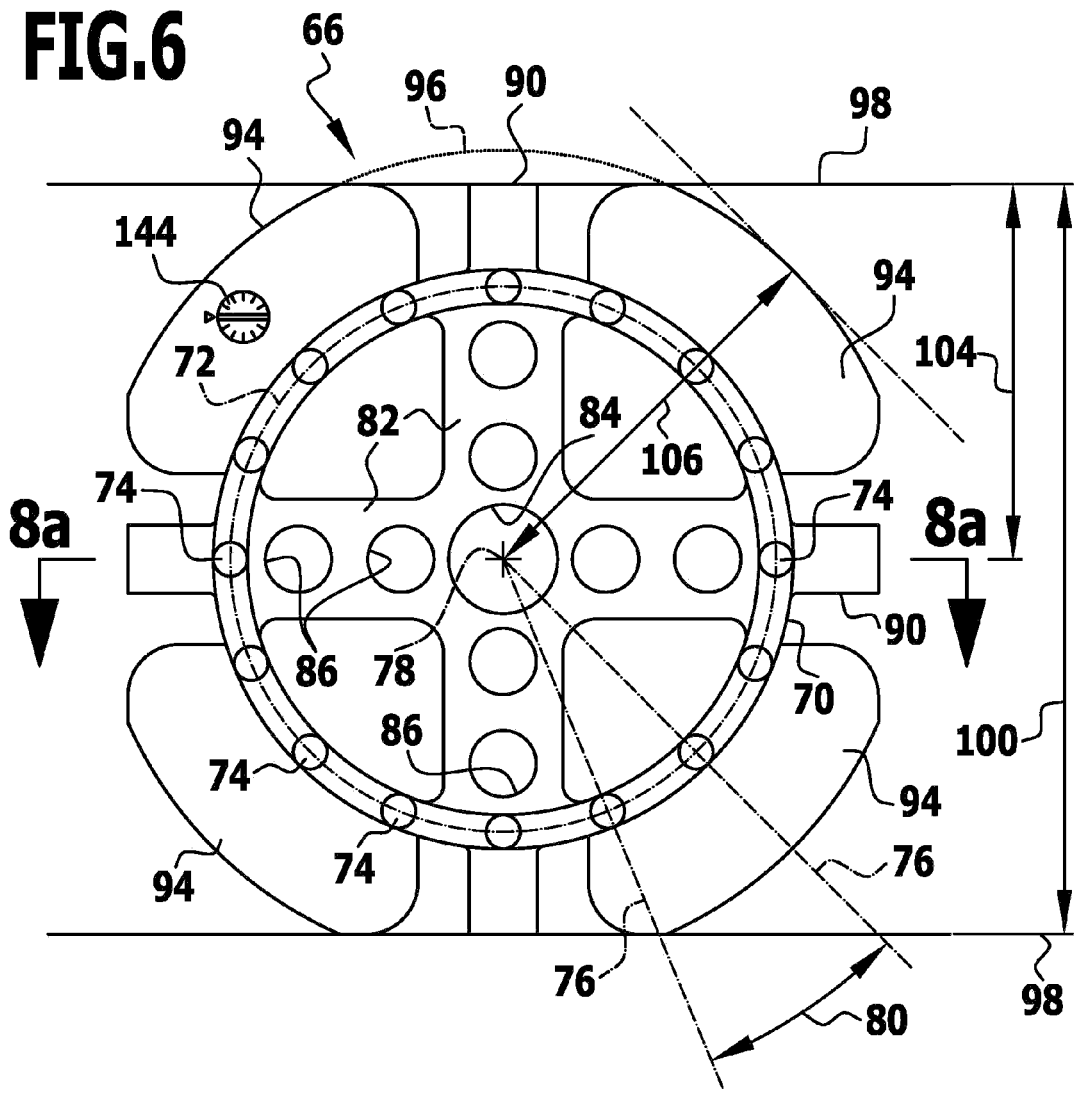
FIG. 6: shows a plan view of a receiving part of a screw container.

A coupling projection 94 projecting radially outwards and having an outer contour 96 in the shape of a circular arc extends between two respective snap-in projections 90, spaced from them. The outer contour 96 is indicated in FIG. 6 by a dash-dot line. Furthermore, the coupling projections 94 are constructed such that a tangent 98 touching the snap-in projections 90 also forms at the same time a boundary line for the coupling projections 94. A distance 100 between two respective, parallel tangents 98 corresponds to a distance 102 of groove bases which point towards one another from grooves 58 and 60 of a screw container receptacle 36 which are associated with one another. As a result, a distance 104 of the tangent 98 from the longitudinal axis 78 is also, therefore, smaller than a radius 106 which is defined by the outer contour 96. This makes it possible to introduce the screw container 38 into a screw container receptacle 36 parallel to one of its webs 82, wherein respective snap-in projections 90 pointing away from one another in opposite directions as well as areas of the coupling projections 94 touching on tangents 98 can engage in the grooves 58 and 60, respectively, and are guided in them. As a result, the screw container 38 may be displaced in the direction towards the longitudinal web 46 until it takes up its storage position, in which the snap-in nose 92 sliding onto the projection 62 during insertion engages in the elongated hole 64 due to the snap-in projection 90 springing back, as is well apparent in FIG. 3, for example.

The screw receptacles 86 serve to accommodate bone screws 108, of which two are illustrated in FIG. 3 by way of example. An external diameter of a screw head of the bone screw 108 is somewhat larger than a diameter of the bores forming the screw receptacles 86 and so a screw body of the bone screw 108 can be introduced into the screw receptacle but an edge thereof forms a stop for the head of the bone screw 108.

So that bone screws 108 inserted into the screw receptacles 86 cannot fall out of the screw receptacles 86 in an unintentional manner, the cover 68 is provided. It comprises a disk-like cover plate 110 as well as a hollow cylindrical annular wall 112 which projects from this and the internal diameter of which is somewhat larger than an external diameter of the basic member 70. As a result, the cover 68 can be pushed over the receiving part 66 from above with the annular wall 112 first.

A coupling pin 114, which protrudes on an underside of the cover plate 110 and is formed by four snap-in projections 116 which bear snap-in noses 118 at their free ends which project radially outwards, serves to connect the cover 68 to the receiving part 66. The coupling pin 114 can be introduced into the bore 84 with the snap-in noses 118 first, whereby the snap-in projections 116 are pivoted in the direction towards a longitudinal axis of the coupling pin 114 and only spring back again into their basic position illustrated in FIG. 8b when the snap-in noses 118 project out of the bore 84 and engage laterally behind it, as is apparent in FIG. 3. It is possible as a result of the design of cover 68 and receiving part 66 to turn there two parts relative to one another about the longitudinal axes 78 and 120, respectively.

Defined rotary positions of the cover 68 relative to the receiving part 66 may be set when a positioning member 122, which is in the shape of a semi sphere and protrudes from an underside of the cover plate 110, engages in one of the sixteen recesses 74. As a result, sixteen defined angular positions of the cover 68 relative to the receiving part may be realized. If the cover is moved out of a defined angular position, the positioning member 122 slides onto the end edge 72 and leads to a temporary deformation of the cover 68 until it can engage in an adjacent recess 74. The positioning member 122 therefore forms a positioning mechanism in conjunction with the recesses 74.

The cover 68 is, furthermore, provided with two removal openings 124 and 126 which are formed by bores and are each arranged on a radial ray 128 and 130, respectively, which form between them an angle 132 of 45°. The removal opening 124 is arranged at a distance from the longitudinal axis 120 so that it can be brought concentrically into congruency with the screw receptacles 86 which are arranged adjacent to the bore 84. The distance of the removal opening 126 from the longitudinal axis 120 is selected such that the removal opening 126 can be brought concentrically into congruency with the screw receptacles 86 which are arranged adjacent to the basic member 70.

The cover 68 has, in addition, wash openings 134 and 136 in the shape of elongated holes, wherein three wash openings 134 are arranged concentrically to the longitudinal axis 120 and have a width in a radial direction which is smaller than an internal diameter of the screw receptacles 86 and their distance from the longitudinal axis 120 corresponds approximately to the distance of the center of the removal opening 124 from the longitudinal axis 120. Five wash openings 136 in the shape of elongated holes are provided in a similar manner concentrically surrounding the longitudinal axis 120, their distance from the longitudinal axis 120 corresponding approximately to the distance of the center of the removal opening 126 from the longitudinal axis 120.

Two tool coupling members 138 which point in a radial direction and are located diametrically opposite one another are arranged on an outer side of the cover 68. They serve as turning aid in order to turn the cover 68 relative to the receiving part 66, for example, by hand or with a screwdriver 26 or a screwdriver handle 28. In FIG. 9, a screwdriver handle 28 is illustrated which has at its proximal end 140 tool receptacles 142 which point in a proximal direction and in each of which a tool coupling member 138 can engage. The screwdriver handle 28 can therefore be pushed onto the cover 68 with its proximal end and the cover 68 can be turned relative to the receiving part 66 as a result of rotation about its longitudinal axis when the receiving part 66 is securely held, for example, when it is located in a screw container receptacle 36 in the storage position.

It is ensured by the special design of the screw container 38 that only one of the two respective removal openings 124 and 126 can be brought into congruency with exactly one of the screw receptacles 86 so that this is accessible for introducing or removing a bone screw 108. This is possible since the two removal openings 124 and 126 are arranged so as to be offset in circumferential direction through the angle 132, the screw receptacles which are at different distances from the longitudinal axis 78 are, on the other hand, arranged on the same radial rays. The removal openings could, of course, in the reverse case also be arranged on the same radial ray and screw receptacles 86 at different distances from the longitudinal axis 78 on radial rays offset through an angle 132.

It is possible as a result of the positioning mechanism described above to bring the cover 68 into sixteen defined positions relative to the receiving part 66, wherein eight of these positions define so-called removal positions, in which one of the two removal openings 124 and 126, respectively, frees exactly one of the eight respective screw receptacles. The other eight defined positions form so-called closure positions, in which the removal openings 124 and 126 each overlap only partially with one of the screw receptacles 86 so that a passage remains but this is so small that a head of the bone screw 108 cannot pass through it. As a result, the bone screws 108 are held securely in the screw container 38 in the eight closure positions, particularly when this is placed upside down, as well.

The screw container 38 illustrated in FIG. 9 takes up a removal position, in which the removal opening 124 frees a screw receptacle 86. If the cover 68 is turned relative to the receiving part 66 through 22.5°, the positioning member 122 again engages in a recess 74 but neither of the two removal openings 124 and 126, respectively, then overlaps a screw receptacle completely. As a result, the screw container 38 takes up a closure position. If the cover 68 is turned in the same direction, on the other hand, through a further 22.5°, the removal opening 126 overlaps a screw receptacle 86. Further turning through 22.5° transfers the screw container 38 from a removal position into a closure position again. As a result of this special positioning mechanism, removal positions and closure positions are passed through alternatingly during rotation of the cover 68, wherein identical respective positions are, in the end result, taken up after turning though 90°, for example, a position of the screw container 38 as illustrated in FIG. 9 again results.

The cover 68 is preferably produced from a transparent material so that it is immediately apparent, in which of the screw receptacles 86 bone screws 108 are contained. A screw code 144 which is arranged on a coupling projection 94 and is produced, for example, by way of laser marking serves to identify the bone screws 108 contained in the screw container 38.

The construction of the screw container 38 comprising numerous openings ensures that bone screws 108 contained therein can be sterilized with the screw container 38. This is also possible, in particular, when the screw container 38 is arranged in the screw container storage device 34 or this is, on the other hand, included in the supply box 10.

The special design of the screw container 38 makes it possible to remove individual bone screws 108 in a selective manner and, if they are not required, to insert them back into the screw container 38. Since the screw container 38 can be sterilized, bone screws 108 which are not required can be sterilized again with the screw container 38 after a successful operation and be made available for the next procedure. Where necessary, the screw container 38 can also be filled again with individual bone screws 108.

The invention claimed is:

1. Surgical screw container, comprising:
   a receiving part having at least two screw receptacles for accommodating at least two bone screws,
   a closure part mounted on the receiving part so as to be movable,
   at least one storage device coupling member for the releasable connection of the surgical screw container to a surgical screw container storage device for at least one surgical screw container, and
   at least two elongated coupling projections projecting from the surgical screw container in opposite directions, said projections being designed to correspond to two elongated and oppositely disposed parallel grooves of at least one screw container receptacle of the surgical screw container storage device and said projections being insertable into the grooves of the at least one screw container receptacle for guidance of the surgical screw container into a storage position in which the at least one storage device coupling member engages with a corresponding coupling member of the surgical screw container storage device,
   wherein:
   the closure part is adapted to be brought into at least one closure position relative to the receiving part, none of the screw receptacles being accessible for insertion or removal of a bone screw in said closure position, and
   the closure part is adapted to be brought from the at least one closure position into at least two removal positions, only a single screw receptacle being accessible for the insertion or removal of a single bone screw in each of said removal positions.

2. Surgical screw container as defined in claim 1, wherein the screw receptacles are designed as insert bores or blind-hole bores in a basic member of the receiving part.

3. Surgical screw container as defined in claim 1, wherein the closure part is mounted on the receiving part so as to be rotatable about an axis of rotation.

4. Surgical screw container as defined in claim 3, wherein longitudinal axes of the screw receptacles extend parallel to the axis of rotation.

5. Surgical screw container as defined in claim 3, wherein the at least two screw receptacles are arranged concentrically around the axis of rotation.

6. Surgical screw container as defined in claim 3, wherein the at least two screw receptacles are arranged on at least two concentric circles around the axis of rotation.

7. Surgical screw container as defined in claim 1, wherein the closure part is adapted to be connected to the receiving part in a snap-in manner so as to be movably mounted thereon.

8. Surgical screw container as defined in claim 1, wherein the receiving part and the closure part each bear a coupling element for the movable mounting on one another, said coupling elements being adapted to be brought into engagement with one another.

9. Surgical screw container as defined in claim 8, wherein the two coupling elements are rotatable relative to one another in a coupling position and are held on one another by means of a snap-in connection.

10. Surgical screw container as defined in claim 8, wherein one of the two coupling elements is a coupling pin and the other of the two coupling elements is a pin receptacle corresponding to the coupling pin.

11. Surgical screw container as defined in claim 10, wherein the coupling pin defines an axis of rotation of the closure part.

12. Surgical screw container as defined in claim 1, wherein the closure part has at least one removal opening which frees a single screw receptacle at least in one of the at least two removal positions.

13. Surgical screw container as defined in claim 12, wherein:
   the closure part has a cover plate for covering the screw receptacles at least partially, and
   the at least one removal opening is designed as a passage in the cover plate.

14. Surgical screw container as defined in claim 13, wherein the passage is a bore.

15. Surgical screw container as defined in claim 12, wherein the at least one removal opening is arranged concentrically around an axis of rotation of the closure part.

16. Surgical screw container as defined in claim 12, wherein in each of the removal positions only one removal opening is adapted to be aligned coaxially with one of the screw receptacles.

17. Surgical screw container as defined in claim 1, further comprising:
   a positioning mechanism comprising a plurality of positioning members for the defined positioning of the closure part in at least one of the at least one closure position and the at least one removal position, wherein:
   at least one of the positioning members is provided on the receiving part and at least one corresponding positioning member is provided on the closure part, and
   at least two positioning members on the closure part and on the receiving part, said positioning members corresponding to one another, engage in one another when at least one removal opening of the closure part frees a single screw receptacle in the at least one removal position.

18. Surgical screw container as defined in claim 17, wherein the positioning members comprise positioning projections and positioning recesses.

19. Surgical screw container as defined in claim 17, wherein the positioning members are arranged concentrically around an axis of rotation of the closure part.

20. Surgical screw container as defined in claim 17, wherein the positioning members are arranged at equal angular distances around an axis of rotation of the closure part.

21. Surgical screw container as defined in claim 17, wherein:
the receiving part has an annular edge pointing in a direction towards the closure part, and
the edge bears the positioning members provided on the receiving part.

22. Surgical screw container as defined in claim 17, wherein at least one positioning member is arranged on an underside of the closure part pointing in a direction towards the receiving part.

23. Surgical screw container as defined in claim 18, wherein:
a number of positioning recesses corresponds to an integral power of the number 2,
a number of positioning projections provided is at the most the same as the number of positioning recesses, and
an angular distance between the positioning recesses corresponds to a quotient of 360° and the number of positioning receptacles.

24. Surgical screw container as defined in claim 12, wherein:
at least two removal openings are provided, said removal openings being arranged on at least two radial rays proceeding from an axis of rotation of the closure part, and
the at least two radial rays form an angle of rotation between them.

25. Surgical screw container as defined in claim 24, wherein the angle of rotation corresponds to an integral multiple of an angular distance between positioning members on at least one of the closure part and on the receiving part.

26. Surgical screw container as defined in claim 24, wherein:
at least two removal openings at different distances from the axis of rotation are provided, and
the angle of rotation formed by the radial rays is 45°, the removal openings being arranged on said radial rays.

27. Surgical screw container as defined in claim 1, wherein:
the at least one storage device coupling member comprises a snap-in element; and
the corresponding coupling member of the surgical screw container storage device comprises a corresponding snap-in element.

28. Surgical screw container as defined in claim 1, wherein several storage device coupling members are provided, said coupling members being distributed uniformly over a circumference of the surgical screw container.

29. Surgical screw container as defined in claim 1, wherein the at least two coupling projections are formed by tongues located in one plane and spaced from one another in a circumferential direction.

30. Surgical screw container as defined in claim 1, wherein the at least one storage device coupling member of the surgical screw container is arranged between two respective coupling projections.

31. Surgical screw container as defined in claim 1, wherein:
four coupling projections and four storage device coupling members are provided, and
an outer contour of the coupling projections is designed to be concentric to an axis of rotation of the closure part.

32. Surgical screw container as defined in claim 1, wherein a distance of a tangent touching two spaced coupling projections from an axis of rotation of the closure part is smaller than a distance of a concentric outer contour of the coupling projections from the axis of rotation.

33. Surgical screw container as defined in claim 1, wherein the closure part has wash openings.

34. Surgical screw container as defined in claim 33, wherein the wash openings are provided in a cover plate of the closure part.

35. Surgical screw container as defined in claim 1, wherein the receiving part comprises a sleeve-like basic member defining a longitudinal direction and at least one web passing through the basic member transversely to the longitudinal direction and bearing the at least two screw receptacles.

36. Surgical screw container as defined in claim 35, wherein at least two intersecting webs are provided and wherein a pin receptacle corresponding to a coupling pin of the closure part is arranged at the point of intersection of the two webs.

37. Surgical screw container as defined in claim 35, wherein the coupling projections project radially outwards from the sleeve-like basic member in a flange-like manner.

38. Surgical screw container, comprising:
a receiving part having at least two screw receptacles for accommodating at least two bone screws, the receiving part comprising a sleeve-like basic member defining a longitudinal direction and at least one web passing through the basic member transversely to the longitudinal direction and bearing the at least two screw receptacles,
a closure part mounted on the receiving part so as to be movable,
at least one storage device coupling member for the releasable connection of the surgical screw container to a surgical screw container storage device for at least one surgical screw container, the at least one storage device coupling member projecting radially outwards from the sleeve-like basic member in a flange-like manner, and
at least two coupling projections projecting in opposite directions, said projections being designed to correspond to two parallel grooves of at least one screw container receptacle of the surgical screw container storage device and being insertable into the grooves, said grooves pointing towards one another,
wherein:
the closure part is adapted to be brought into at least one closure position relative to the receiving part, none of the screw receptacles being accessible for insertion or removal of a bone screw in said closure position, and
the closure part is adapted to be brought from the at least one closure position into at least two removal positions, only a single screw receptacle being accessible for the insertion or removal of a single bone screw in each of said removal positions.

39. Surgical screw container as defined in claim 1, wherein the closure part has at least one tool coupling member for an actuating tool for turning the closure part relative to the receiving part.

40. Surgical screw container as defined in claim 39, wherein the at least one tool coupling member is a projection projecting from a cover plate of the closure part.

41. Surgical screw container as defined in claim 39, wherein two tool coupling members located diametrically opposite one another in relation to an axis of rotation of the closure part are provided.

42. Surgical screw container as defined in claim 1, wherein the surgical screw container is produced from a sterilizable plastic.

43. Surgical screw container as defined in claim 1, wherein the closure part is produced from a transparent material.

44. Surgical screw container as defined in claim 1, wherein a bone screw is arranged in each screw receptacle.

45. Surgical screw container storage device for at least one surgical screw container, comprising:
- at least one screw container receptacle, at least one surgical screw container being insertable into said receptacle at least partially, each of said at least one screw container receptacles comprising:
  - a storage device coupling member for coupling with at least one corresponding storage device coupling member of said at least one surgical screw container,
  - two elongated and oppositely disposed parallel grooves which correspond to at least two elongated coupling projections projecting from the surgical screw container in opposite directions, said grooves being adapted to accept said projections for guidance of the surgical screw container into a storage position in which the storage device coupling member of the surgical screw container engages with the corresponding coupling member of the at least one screw container receptacle,
- wherein each of said at least one surgical screw container comprises:
  - a receiving part having at least two screw receptacles for accommodating at least two bone screws,
  - the at least two elongated coupling projections,
  - a closure part mounted on the receiving part so as to be movable, and
  - the at least one storage device coupling member for the releasable connection of the surgical screw container to the surgical screw container storage device for the at least one surgical screw container,
  - the closure part is adapted to be brought into at least one closure position relative to the receiving part, none of the screw receptacles being accessible for insertion or removal of a bone screw in said closure position, and
  - the closure part is adapted to be brought from the at least one closure position into at least two removal positions, only a single screw receptacle being accessible for the insertion or removal of a single bone screw in each of said removal positions.

46. Surgical screw container storage device as defined in claim 45, wherein the at least one surgical screw container is adapted to be pushed into the screw container receptacle.

47. Surgical screw container storage device as defined in claim 45, further comprising the at least one surgical screw container.

48. Surgical screw container storage device as defined in claim 45, wherein the at least one surgical screw container is connectable to the screw container storage device in a snap-in manner.

49. Surgical screw container storage device as defined in claim 48, wherein the at least one surgical screw container is connected to the screw container storage device in a storage position, the at least one surgical screw container being introduced completely into the screw container receptacle in said storage position.

50. Surgical screw container storage device as defined in claim 49, wherein the storage device coupling member of the screw container receptacle and the corresponding at least one storage device coupling member of said at least one surgical screw container being in engagement in the storage position.

51. Surgical screw container storage device as defined in claim 50, wherein one of the two corresponding storage device coupling members is designed as a snap-in element in a form of a flexibly mounted snap-in nose and the other storage device coupling member is designed as a snap-in element in a form of a recess interacting with the snap-in nose.

52. Surgical screw container storage device as defined in claim 50, wherein a storage device coupling member is associated with each screw container receptacle.

53. Surgical screw container storage device as defined in claim 45, wherein the screw container receptacles comprise coupling receptacles in the form of two parallel grooves pointing towards one another, corresponding coupling projections of the at least one surgical screw container being insertable into said grooves.

54. Surgical supply box for at least one of surgical implants and surgical tools, comprising:
- several compartments for accommodating at least one of surgical implants, surgical instruments, and surgical tools, at least one of the compartments being adapted for accommodating a screw container storage device for at least one surgical screw container,
- the screw container storage device comprising at least one screw container receptacle, the at least one surgical screw container being insertable into said receptacle at least partially, and
- said surgical screw container comprising:
  - a receiving part having at least two screw receptacles for accommodating at least two bone screws,
  - a closure part mounted on the receiving part so as to be movable,
  - at least one storage device coupling member for the releasable connection of the surgical screw container to the screw container storage device for at least one surgical screw container, and
  - at least two elongated coupling projections projecting from the surgical, screw container in opposite directions, said projections being designed to correspond to two elongated and oppositely disposed parallel grooves of the at least one screw container receptacle of the screw container storage device and said projections being insertable into the grooves of the screw container receptacle for guidance of the surgical screw container into a storage position in which the at least one storage device coupling member engages with a corresponding coupling member of the at least one screw container receptacle,
- wherein:
  - the closure part is adapted to be brought into at least one closure position relative to the receiving part, none of the screw receptacles being accessible for insertion or removal of a bone screw in said closure position, and
  - the closure part is adapted to be brought from the at least one closure position into at least two removal positions, only a single screw receptacle being accessible for the insertion or removal of a single bone screw in each of said removal positions.

55. Surgical supply box as defined in claim 54, wherein the supply box has at least one receptacle for a screwdriver and a screwdriver handle.

56. Surgical supply box as defined in claim 54, wherein:
- the supply box comprises at least one screwdriver and a screwdriver handle having a proximal end, and
- the proximal end bears a tool receptacle for engagement with a tool coupling member of the closure part of said surgical screw container.

57. Surgical supply box as defined in claim 56, wherein the tool receptacle comprises at least two recesses located diametrically opposite one another and pointing in a proximal direction.

58. Surgical supply box as defined in claim 54, wherein at least some of the compartments are designed to essentially correspond to an outer contour of the implants, instruments, tools or screw container storage devices stored therein.

* * * * *